United States Patent [19]

Burger et al.

[11] Patent Number: 5,472,950
[45] Date of Patent: Dec. 5, 1995

[54] COMPOSITIONS CONTAINING COBALT HYALURONIC ACID COMPLEX

[75] Inventors: Kalman Burger, Budapest; Ivan Rethey, deceased, late of Budapest, by Ágota Réthey-Prikkel née Fónagy, legal representative; Bela Stefko, Budapest; Istvan Gebhardt, Budapest; Arpadne Kiraly nee Gyongyver Soos, Budapest; Geza T. Nagy, Budapest; Janos Illes, Budapest; Erzsebet Nesmelyi, Budapest; Istvan Racz, Budapest; Viktoria Varkonyi, Budapest, all of Hungary

[73] Assignee: Richter Gedeon Vegyeszeti Gyar Rt., Budapest, Hungary

[21] Appl. No.: 949,030

[22] Filed: Sep. 22, 1992

Related U.S. Application Data

[63] Continuation-in-part of Ser. No. 928,154, Aug. 10, 1992, which is a continuation-in-part of Ser. No. 602,326, Nov. 21, 1990, abandoned.

[30] Foreign Application Priority Data

Feb. 24, 1989 [HU] Hungary ................................. 891/89
Feb. 20, 1990 [WO] WIPO ..................... PCT/HU90/00013

[51] Int. Cl.$^6$ .......................... A61K 31/70; C07M 23/00
[52] U.S. Cl. ..................... 514/54; 536/55.1; 536/121
[58] Field of Search .................. 536/55.1, 121; 514/54

[56] References Cited

U.S. PATENT DOCUMENTS

| | | | |
|---|---|---|---|
| 4,225,592 | 9/1980 | Lakatos et al. | 536/121 |
| 4,623,539 | 11/1986 | Tune | 424/79 |
| 4,736,024 | 4/1988 | Dalla Valle et al. | 536/55.3 |

OTHER PUBLICATIONS

Torvard Laurent; "The Biology of Hyaluronan"; Ciba Foundation Symposium 143; 1989 John Wiley & Sons; 5 pages.

*Primary Examiner*—Douglas W. Robinson
*Assistant Examiner*—Elli Peselev
*Attorney, Agent, or Firm*—Herbert Dubno; Jonathan Myers

[57] ABSTRACT

Complexes of deprotonated hyaluronic acid with 3$d$ metal ions of the 4th period of the Periodic Table and compositions containing these complexes as active ingredients or carriers. A process for the preparation of the complexes and compositions (pharmaceutical and cosmetic compositions) containing these complexes as active ingredients are disclosed in which zinc or cobalt (II) hyaluronate is preferably used as active ingredient.

3 Claims, 3 Drawing Sheets

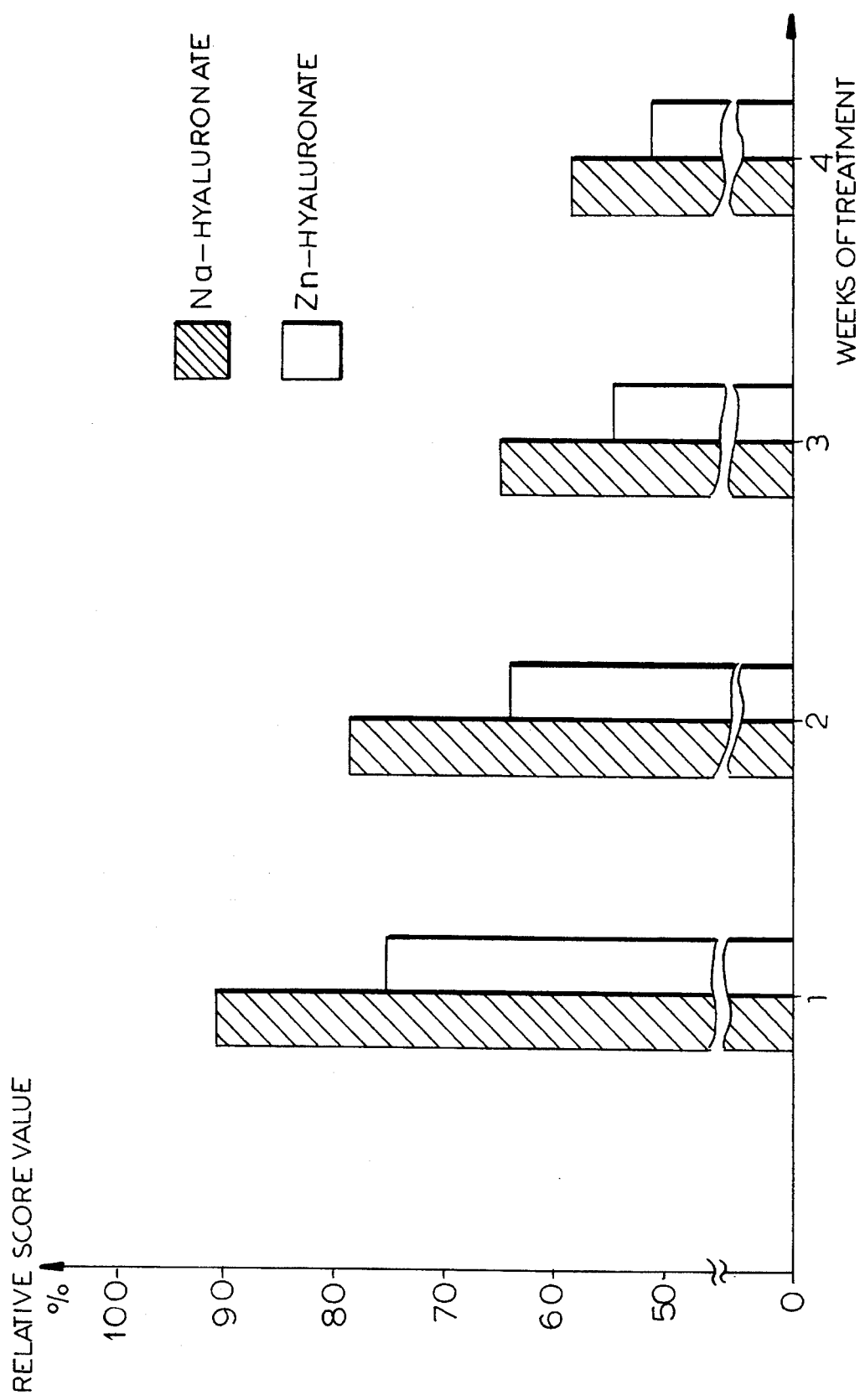

COMPOSITIONS CONTAINING COBALT HYALURONIC ACID COMPLEX

CROSS REFERENCE TO RELATED APPLICATIONS

This application is a Continuation-in-Part of copending application Ser. No. 07/928,154 filed 10 Aug. 1992 as continuation of then copending application Ser. No. 07/602,326 filed 21 Nov. 1990 as a National Phase application of PCT/HU90/00013 filed 20 Feb. 1990 and based upon Hungarian national application Ser. No. 891/89 of 24 Feb. 1989 under the International Convention.

FIELD OF THE INVENTION

This invention relates to novel hyaluronic acid associates (complexes) of 3d metal ions of the 4th period of the Periodic Table, with a stoichiometric composition, prepared through the interaction of equivalent amounts of an alkali metal hyaluronate, alkaline earth metal hyaluronate, silver hyaluronate or a quaternary ammonium hyaluronate and 3d metal ions in aqueous solution, and to pharmaceutical compositions containing these associates (complexes) as active ingredients.

The invention further relates to a process for the preparation of these novel associates (complexes) and compositions containing these associates (complexes) as active ingredients.

According to a particularly preferred embodiment of the process of the present invention, the aqueous solutions containing the novel hyaluronic acid associates (complexes) of 3d metal ions of the 4th period of the Periodic Table, with a stoichiometric composition, prepared through the interaction of equivalent amounts of sodium hyaluronate, and 3d metal ions in aqueous solution, are prepared directly from an aqueous solution of sodium hyaluronate.

The novel associates according to the present invention mainly involve zinc and cobalt hyaluronate. The compositions containing these latter associates may be pharmaceutical (therapeutical) or cosmetic and optionally other compositions. The compositions containing the novel associates according to the invention are therapeutically effective for e.g.: the acceleration of epithelization of epithelium-deficient body surfaces; healing of crural ulcers, decubitus (bed-ulcers), primarily not healing wounds, burns, radiation- or heat-induced wounds, vulgar acne and conglobated acnes, although they can be used in other areas, too.

BACKGROUND OF THE INVENTION

Hyaluronic acid is a macromolecule known for more than 50 years and which has first been described by Meyer et al. [J. Biol. Chem. 107, 629 (1954); J. Biol. Chem. 114, 689 (1936)]. The structure determination was performed by Weissman et al. [J. Am. Chem. Soc. 76, 1753 (1954)]. Hyaluronic acid is a highly viscous native glucosaminoglycan containing alternating $\beta_{1-3}$ glucouronic acid and $\beta_{1-4}$ glucosamine moieties; its molecular weight is between 50000 and several (8 to 13) millions. The recovery of hyaluronic acid is an old task. The separation and use of an extra pure hyaluronic acid are described e.g. in the U.S. Pat. Nos. 4,141,973 and 4,303,676 and in the European Patent No. 0 144 019. Until recently hyaluronic acid has been employed as the sodium salt e.g. in therapy, mainly in opthalmology, surgery and cosmetics. The salts of hyaluronic acid formed with alkali, alkaline earth, magnesium, aluminum, ammonium or substituted ammonium ions may serve as carriers for promoting the absorption of drugs (see the Belgian Patent Specification No. 904,547). Heavy metal salts of hyaluronic acid (wherein "heavy metals" mean the elements of the 5th, 6th and 7th periods of the Periodic Table as well as the lanthanides and actinides) and within these the silver salt are utilized as fungicidal agents whereas the gold salt is employed for the treatment of arthritis (see the patent specification WO 87/05517).

It has been proven by various structure-elucidating methods that the secondary structure, i.e. the conformation of hyaluronic acid is changed by binding metal ions [W. T. Winter and A. Struther: J. Mol. Biol. 517, 761 (1977); J. K. Sheehan and E. D. T. Atkins: Int. J. Biol. Macromol. 5, 215 (183); and N. Figueroa and B. Chakrabarti: Biopolymers 17, 2415 (1978)]. Significantly varying effects on the molecular structure can be exerted even by metal ions of similar character as shown by comparative X-ray study of potassium and sodium hyaluronate [A. K. Mitra et al.: J. Macromol., Sci. Phys. 824, 1 and 21 (1985)]. This is all the more valid for compounds of hyaluronic acid formed with metal ions of various sorts bearing various charges.

No reference relating to hyaluronic acid associates (complexes) of 3d metal ions of the 4th period of the Periodic Table, with a stoichiometric composition, prepared through the interaction of equivalent amounts of an alkali metal hyaluronate, alkaline earth metal hyaluronate, silver hyaluronate or a quaternary ammonium hyaluronate and 3d metal ions in aqueous solution, can be found in the literature. Actually, according to gel filtration chromatography examinations, hyaluronic acid, in contrast with heparin, is unable to bind zinc ions [(R. F. Parish and W. R. Fair: Biochem. J. 193, 407 to 410 (1981)].

In spite of the fact that, according to the literature, hyaluronic acid (or its sodium salt) is unable to bind zinc ions, we undertook to investigate the coordination chemistry of the interaction between hyaluronic acid and 3d metal ions of the 4th period of the Periodic Table and among these, chiefly, zinc and cobalt ions. Since hyaluronic acid is nearly exclusively commercialized as its sodium salt thus being the basic substance of all systems containing hyaluronate, our investigations were begun on the interaction of sodium ions and hyaluronate. For this purpose the free sodium ion activity of aqueous sodium hyaluronate solutions was measured by using a sodium selective glass electrode. It was unambiguously found from these measurements that not more than 60% of sodium ions introduced as equivalent together with the carboxylate groups of hyaluronate are present as free ions in the aqueous solutions whereas the remainder of 40% is in a form bound to the hyaluronate.

According to our measurements, by increasing the sodium ion concentration the amount of the sodium ions bound can be raised to 50–55% calculated for all available carboxylate groups. Thus, it has been verified that, as contrasted with common properties of salts, sodium hyaluronate is not completely dissociated in aqueous solution.

DESCRIPTION OF THE INVENTION

In the next step of our investigations an aqueous solution of sodium hyaluronate was titrated with zinc chloride solution by using a sodium ion-selective electrode as mentioned above for following the change in the activity of free sodium ions in the system. A characteristic curve reflecting the process is shown in FIG. 1. It is perceivable that sodium ions originally bound to hyaluronate are liberated on the effect of zinc ions. Based on the results of these measurements the total sodium ion concentration is liberated by an equivalent amount of zinc, a fact unequivocally proving that zinc ions are more strongly bound to hyaluronate than are sodium ions. Thus, the earlier statement that hyaluronic acid would be unable to bind zinc ions [R. F. Parrish and W. R. Fair: Biochem. J. 193, 407 (1981)] has experimentally been refuted.

Thereby, knowledge previously held by workers skilled in the art was disproved.

From our investigations discussed above it became clear that, through the interaction of equivalent amounts of sodium hyaluronate and zinc ions (zinc chloride) in aqueous solution a zinc hyaluronate associate with a stoichiometric composition is formed. After an appropriate isotonization the solution obtained can directly be used for therapeutical purposes and the zinc compound need not be prepared in solid state in a separate process.

Nevertheless, the complex was prepared in a solid state for characterization and the direct environment of the zinc ion was determined by using the "Extended X-ray Absorption Fine Structure" (EXAFS) method. It has been found that zinc is surrounded by four oxygen atoms in the first coordination sphere. The length of the Zn—O bond distances is 199 pm whereas two carbon atoms are present in a longer distance of 241 pm from the zinc atom.

According to our examinations zinc hyaluronate significantly differs from the analogous copper complex which latter contains four equatorial and two axial Cu—O bonds with the values of 194 and 234 pm, respectively. The distance between the copper atom and the new two carbon atoms is 258 pm. The structure of the cobalt (II) complex is similar to the zinc complex but not to the copper complex; specifically the Co—O bond distance is 197 pm±1.0 and the Co—C is 239 pm ±1.5 pm.

The present invention relates to hyaluronic acid associates (complexes) of 3d metal ions of the 4th period of the Periodic Table, with a stoichiometric composition, prepared through the interaction of equivalent amounts of alkali metal hyaluronate, alkaline earth metal hyaluronate, silver hyaluronate or a quaternary ammonium hyaluronate and 3d metal ions in aqueous solution.

The invention further relates to a pharmaceutical composition containing as active ingredient hyaluronic acid associates (complexes) of 3d metal ions of the 4th period of the Periodic Table, with a stoichiometric composition, prepared through the interaction of equivalent amounts of an alkali metal hyaluronate, alkaline earth metal hyaluronate, silver hyaluronate or a quaternary ammonium hyaluronate and 3d metal ions in aqueous solution, optionally in admixture with a carrier and/or other active ingredients and/or additives.

According to another aspect of the invention, there is provided a process for the preparation of the novel associates (complexes) of the invention, with a stoichiometric composition, which comprises:

a) adding an aqueous solution containing the equivalent amount of a salt, preferably the chloride of one of the 3d metal ions of the 4th period of the Periodic Table, to an equivalent amount of an aqueous solution of sodium hyaluronate or to an equivalent amount of another salt (alkali or alkaline earth metal salt, optionally silver salt) of hyaluronate; or b) dissolving an associate formed from hyaluronic acid with a quaternary ammonium salt in an aqueous suspension in a solvent couple containing the aqueous solution of an equivalent amount of a 3d metal ion of the 4th period of the Periodic Table and a solvent which is precipitating the hyaluronic acid associates (complexes) of 3d metal ions of the 4th period of the Periodic Table, as stoichiometric compositions, by an alkanol or alkanone in a known manner, or separating the precipitate from the solution and then, if desired drying it under mild conditions.

This process serves for the preparation of aqueous solutions containing as active ingredient a stoichiometric composition which is a zinc or cobalt (II) hyaluronate associate (complex) or a similar associate of a 3d metal ion of the 4th period of the Periodic Table, respectively. These solutions were in each case prepared by the direct reaction of the metal ion with the hyaluronate component. This method of preparation made unnecessary to previously separate the active ingredients mentioned above in a solid state. In the solution prepared by using the process of the invention the amount of free (metal-unbound) hyaluronate is negligible even in the presence of an equivalent amount of zinc. In the presence of an excess of zinc ions the formation of the zinc hyaluronate associate (complex) becomes quantitative.

In the course of preparation of the metal associates as discussed above the pH remains at a value of about 4.5 to 6.5. In the case of a 0.2% by weight/volume (wt./vol.) hyaluronate solution the pH reaches a value of 5.4 whereas in the case of 0.5% by wt./vol. the pH value is 5. When necessary, the pH of the latter system can be adjusted to a value of 5.5 to 5.6 by adding a few drops of isotonic sodium acetate solution.

Solutions of two sorts containing zinc hyaluronate as active ingredient have been prepared by using the process discussed above.

1. Zinc hyaluronate solution made isotonic by an excess of zinc chloride;

Taking into consideration that free zinc chloride alone may also preferably be used in the dermatology, the osmotic pressure of the zinc hyaluronate solution was adjusted to the isotonic value by using an excess of zinc chloride. The solution thus obtained did not contain any free (zinc-unbound) hyaluronate at all but an excess of zinc chloride was present in the system together with zinc hyaluronate.

2. Zinc hyaluronate solution made isotonic by a monosaccharide or a sugar alcohol:

For a therapeutic use wherein the presence of hyaluronate-unbound zinc ions is not indicated, the stoichiometric solution containing zinc ions in an amount equivalent to the hyaluronate was made isotonic by using a polyalcohol (sugar alcohol, preferably sorbitol) or a mono- or disaccharide (preferably glucose). The free zinc ion and free hyaluronate content of these latter systems did not reach 5% of the total zinc or total hyaluronate content, respectively.

In the course of utilizing the associates according to the invention ion-free compositions may eventually be required. Namely, the associates prepared according to the above process of the invention usually contain sodium chloride or another salt formed from the starting hyaluronate cation and the anion of the 3d metal salt.

Two different process variants can be used for the preparation of a salt-free hyaluronic acid associate formed with a 3d metal ion. These are as follows.

a) A solution of a quaternary ammonium salt is portionwise added to the solution of a known hyaluronate, preferably sodium hyaluronate. After a satisfying purification, the novel quaternary ammonium hyaluronate associate precipitated is dissolved under vigorous stirring in a solvent couple consisting of an aqueous solution of a 3d metal ion of the 4th period of the Periodic Table and a solvent which separate, then the hyaluronate associate is precipitated by adding an alkanol or alkanone to the aqueous phase, the precipitate is separated and washed; or b) after adding 2.0 to 3 volumes of a $C_{1-3}$alkanol or $C_{3-4}$alkanone under stirring to a zinc hyaluronate solution, suitably to a not isotonized solution containing zinc chloride in an amount equivalent to the hyaluronate, the zinc hyaluronate precipitated is filtered and washed with the alkanol or alkanone, respectively used for the precipitation. When necessary, the zinc hyaluronate is dissolved in ion-free water and the precipitation is repeated.

When a solid ion-free zinc hyaluronate is needed, the precipitate is dried under reduced pressure under mild conditions. In the case of a demand on an ion-free zinc hyaluronate solution it is preferable to dissolve the zinc hyaluronate made free from the solvent. According to any of both process variants an ion-free solid or dissolved product is obtained with an optional purity depending on the quality of the starting zinc hyaluronate.

BRIEF DESCRIPTION OF THE DRAWINGS

FIG. 3 is a series of bar graphs showing the severity of crural ulcers treated with sodium hyaluronate and zinc hyaluronate, respectively, over periods of 1, 2, 3 and 4 weeks.

The results of the clinical-pharmacological investigation on a composition (Example 13) containing as active ingredient the zinc hyaluronate according to our invention are shown on a crural ulcer treatment used for the acceleration of epithelization of epithelium-deficient surfaces. A composition containing sodium hyaluronate was used as control.

This examination was carried out on 12 or 14 ulcers, respectively of 8 or 12 patients suffering from crural ulcer. The distribution of the patients of both groups according to sex and age as well as to the nature of the disease was as follows.

| Active Ingredient | No. of Patients | Woman | Man | Average Age | No. of Ulcers Treated | Character of the Ulcer* A | V | M |
|---|---|---|---|---|---|---|---|---|
| Zinc hyaluronate | 12 | 10 | 2 | 63.9 | 14 | 2 | 9 | 1 |
| Sodium hyaluronate | 8 | 6 | 2 | 65.7 | 12 | — | 7 | 1 |

*A = arterial; V = venous; M = Mixed

The treatments were performed in such a way that before beginning the treatment a purifying therapy was carried out according to the actual clinical state of the ulcer. The treatment with zinc or sodium hyaluronate, respectively, was commenced on ulcers nearly purified or in cases where a significant diminution of the sorbes was observed. The treatment was carried out daily once in such a way that the composition was dropped onto the surface of the purified ulcer in am amount wetting the surface of the wound with a thin layer.

The composition was used for 4 weeks. At the beginning of the treatment and then once in a week the data sheet was filled out and the ulcers of the patients were documented by photographs. A discharge sample was taken for bacteriological examination.

The characteristics as well as the severity of the epithelial lesions were marked with the following symbols and scores.

| Characteristics | Severity |
|---|---|
| Area (a) | |
| 0 | 0 |
| Below 10 cm² | 1 |
| Between 10 cm² and 25 cm² | 2 |
| Above 25 cm² | 3 |
| Infectedness (b) | |
| Clinically pure | 0 |
| Coated in 50% | 1 |
| Coated in 100% | 2 |
| Necrosis (c) | |
| (only in the case of an arterial ulcer) | |
| negative | 0 |
| Below 10% | 1 |
| Between 10% and 15% | 2 |
| 100% | 3 |
| No necrosis | 4 |

EVALUATION

For evaluation the values of the separate characteristics were determined and the general severity score was calculated by using the following formula:

$$s = a \times b \times c$$

Figure 1:
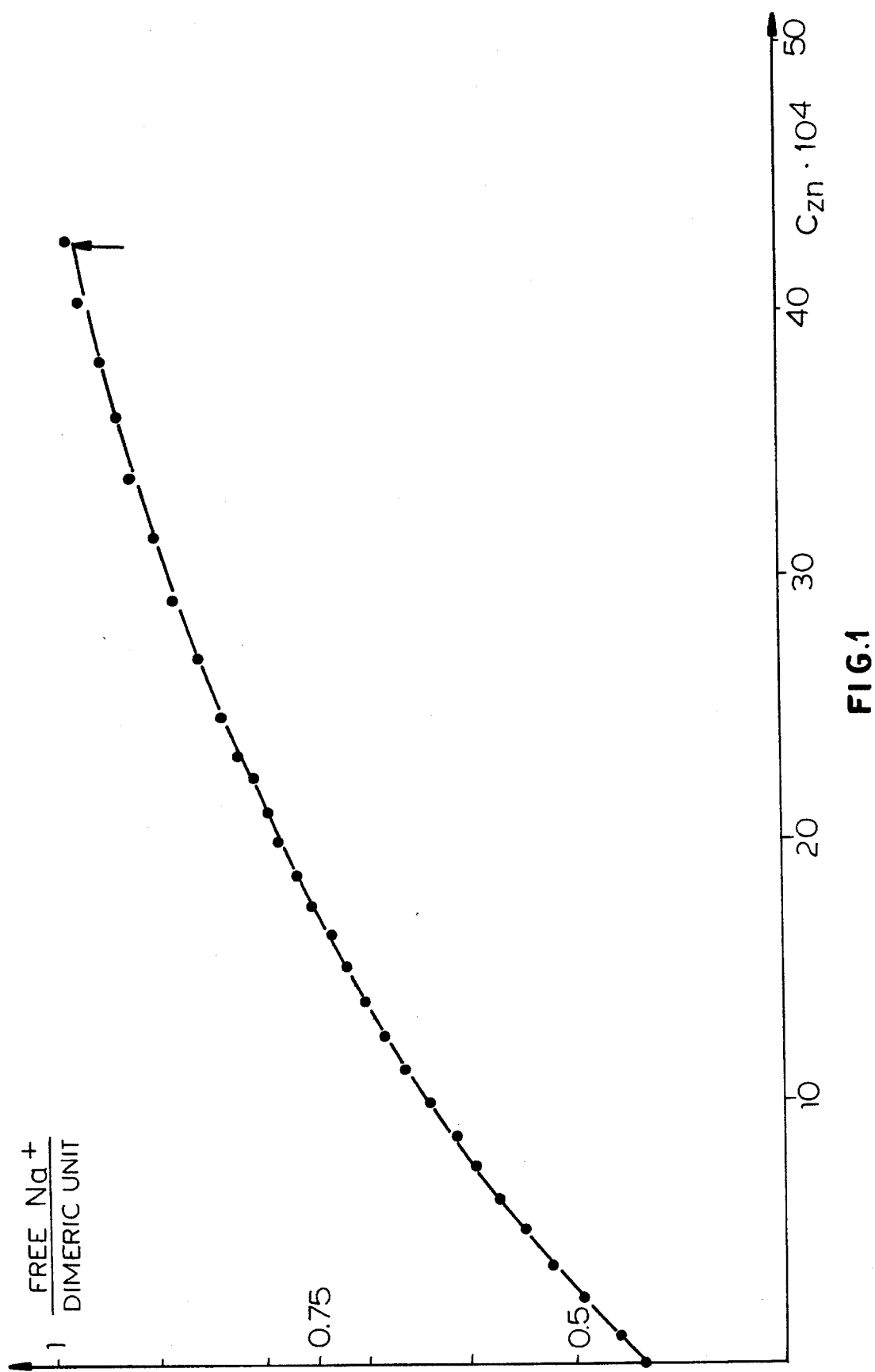
FIG. 1 is a titration curve showing the titration of an aqueous sodium hyaluronate solution with zinc
Figure 2:
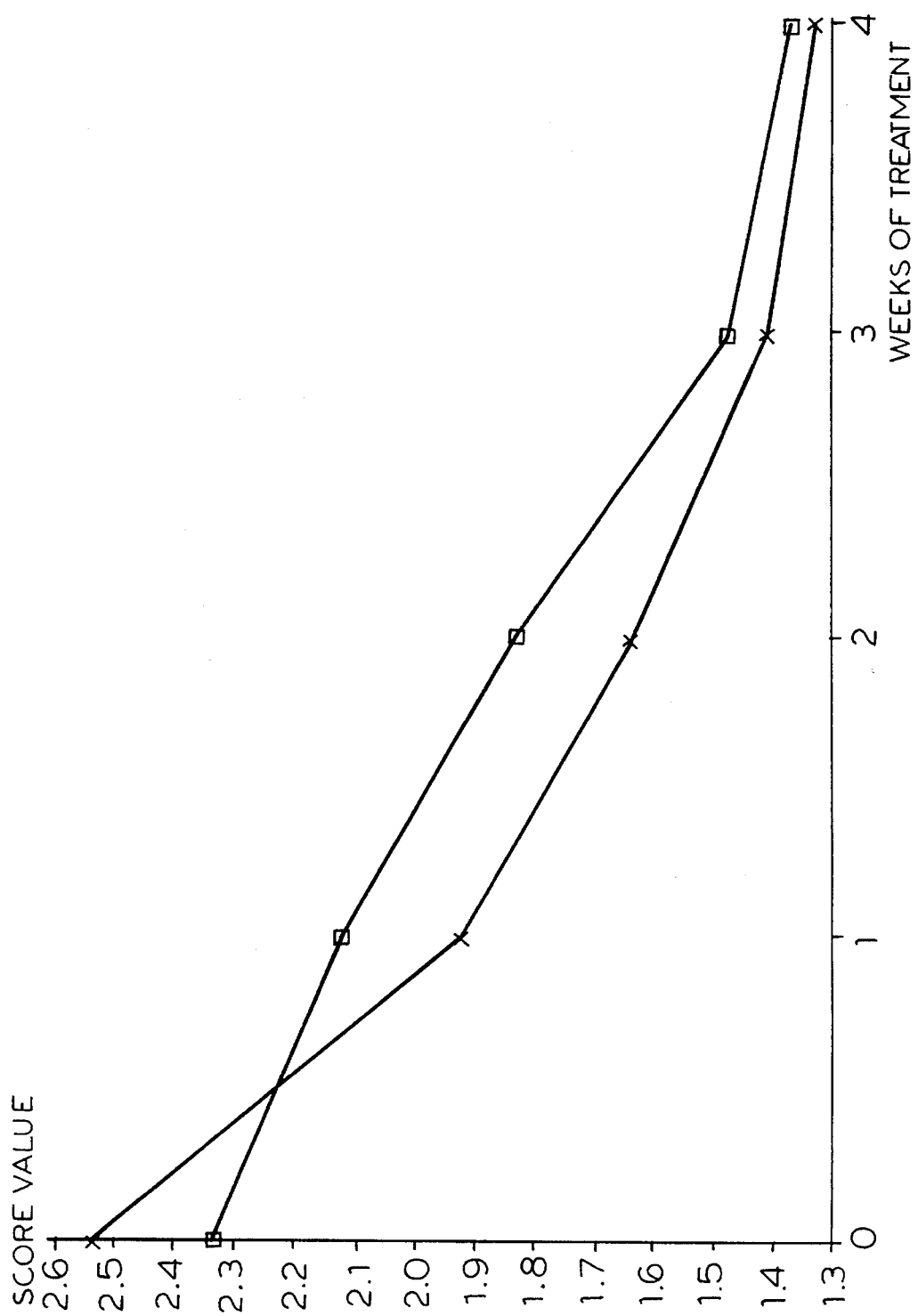
FIG. 2 is a series of two graphs showing the results of the clinical treatment of patients suffering from crural ulcers using zinc hyaluronate according to the curve marked with a cross and using sodium hyaluronate using the curve marked with a square. The x-axis shows the duration of treatment and the y-axis shows the severity of the disease.

The results of the clinical pharmacological investigations are illustrated in FIG. 2. The results of the treatment with zinc hyaluronate is shown on the curve marked with a cross whereas that of the treatment with sodium hyaluronate is illustrated on the curve denoted with a square as a function of the number of weeks involving the treatment. The score value plotted on the ordinate represents the general severity index calculated by using the above formula.

For a more correct comparison of zinc hyaluronate to sodium hyaluronate used as control the relative correct values related to the starting score values as 100% are illustrated in FIG. 3.

The change in the relative correct values was statistically evaluated as a function of number (1 to 4) of weeks. On the zinc and sodium hyaluronate treatment, the number of ulcers decreased below a relative score value of 90%, 80%, 70% and 60%, respectively after 1, 2, 3 and 4 weeks was investigated. The results are summarized in Table 1.

TABLE 1

|  | 1st week | | 2nd week | | 3rd week | | 4th week | |
|---|---|---|---|---|---|---|---|---|
|  | Distribution of the relative score value | | | | | | | |
| Active ingredient | 90% | | 80% | | 70% | | 60% | |
| of the composition | below | above | below | above | below | above | below | above |
| Zinc hyaluronate | 12 | 2 | 11 | 3 | 11 | 3 | 11 | 3 |
| Sodium hyaluronate | 4 | 8 | 7 | 5 | 6 | 6 | 3 | 9 |

It can be stated from Table 1 that the treatment with zinc hyaluronate was in every week advantageous in comparison to the results obtained with sodium hyaluronate used as control.

The statistical analysis of the response obtained for the hypothesis in question proved that the advantage of the zinc hyaluronate composition was highly significant (p. 99%) in comparison to sodium hyaluronate.

In a further statistical working-up, a more detailed distribution of the relative score values was investigated as a function of the time of treatment. The results obtained are summarized in Table 2.

TABLE 2

| Active ingredient of the composition | Number and score value of the ulcers | | | |
|---|---|---|---|---|
|  | above 90% | between 90 and 70% | between 70 and 50% | below 50% |
| 1st week | | | | |
| Zinc hyaluronate | 2 | 7 | 5 | 0 |
| Sodium hyaluronate | 8 | 3 | 0 | 1 |
| 2nd week | | | | |
| Zinc hyaluronate | 0 | 6 | 7 | 1 |
| Sodium hyaluronate | 4 | 3 | 5 | 0 |
| 3rd week | | | | |
| Zinc hyaluronate | 0 | 1 | 8 | 2 |
| Sodium hyaluronate | 2 | 5 | 5 | 1 |
| 4th week | | | | |
| Zinc hyaluronate | 2 | 1 | 7 | 3 |
| Sodium hyaluronate | 1 | 5 | 3 | 3 |

The data of Table 2 similarly support the advantage of zinc hyaluronate. The more detailed statistical examinations show the significance to decrease depending on the time of treatment.

Summing up: on an evaluation of the clinical-pharmacological investigations the higher efficiency of zinc hyaluronate could be proven even at a low number of ulcers; this advantage could particularly be supported in the starting period of the treatment.

Microbiological examination of solutions were carried out. The solutions contained either zinc hyaluronate (Zn—HY) prepared according to the present invention, sodium hyaluronate (Na—HY) obtained as HEALON™ (Pharmacia), or Na—HY containing zinc ions prepared according to Example 5 of Czech Inventor's Certificate 264,719.

The following example shows preparation of a 0.1% aqueous solution of Zn—HY according to the present invention:

EXAMPLE A

Preparation of a zinc hyaluronate solution 40.18 mg of sodium hyaluronate are dissolved in 20.0 ml of twice distilled water. Thus, the starting concentration of hyaluronic acid is 2.009 mg/ml, the equivalent concentration of the solution is $4.241 \times 10^3$ mol/liter ($Na^+$ or hyaluronic acid dimer unit). In the course of the measurement, a zinc chloride solution of 0.05154 mol/liter concentration is added to the reaction mixture through a microburet. The solution is first added in little portions (0.05 ml) and then in larger portions (0.1 to 0.2 ml). The potential change in the solution is measured by using a precision potentiometer with digital display and sodium-selective glass and silver/silver chloride electrodes. The titration is continued until the potential measured is not further changed by adding an additional portion of the titrating solution. (The measuring system was calibrated under conditions analogous to the practical measurement). A 0.1% aqueous solution of zinc hyaluronate was obtained.

The selectivity of the sodium ion-selective electrode was observed also in the presence of $Zn^{2+}$ ions in order to control that the potential change in the practical measurement was caused by the liberated $Na^+$ ions and not the $Zn^{2+0}$ ions introduced to the solution. A $2.00 \times 10^{-3}$ M sodium chloride solution was titrated by using the zinc chloride titrating solution under conditions similar to the above conditions. On increasing the concentration of $Zn^{2+}$ from 0 up to $4 \times 10^{-3}$ mol/liter a potential increase of about 2 mV was observed whereas the practical measurement showed a change of about 20 mV under similar conditions. Thus, the evaluation had no obstacle. In the course of measurement the increase in the sodium ion Preparation of a zinc chloride solution since a solution containing zinc chloride in an accurate concentration cannot be prepared by direct weighing-in, first a solution with the nearly desired concentration is prepared. On preparing this solution no acid should be used thus it may occur that the zinc chloride weighed in will not completely be dissolved. After sedimentation of the insoluble residue (about 30 minutes) the volumetric flask is filled up to the mark and the solution is filtered through a filter paper.

The accurate concentration of the filtrate is determined by complexometric titration by using buffer of pH 10 and eryochrom black-T indicator. The zinc chloride solution with an accurate concentration of 0.100 mol/liter is prepared by the precise dilution of this solution.

The characteristics of sodium hyaluronate used for the preparation of solution are as follows:

| Molecular weight | 1850000 daltons |
|---|---|
| Protein content | 0.07% by wt. |
| UV absorption | |
| $A_{257}^{1\%}$ | 0.133 |
| $A_{280}^{1\%}$ | 0.075 |
| Viscosity $[\eta]_{25° C.}^{c \to 0\%}$ | 13.7 dl/g |

| | |
|---|---|
| HA* | 98.12% by wt. |

*HA = hyaluronic acid (as abbreviated herein).

The following example shows preparation of a 0.1% aqueous solution of sodium hyaluronate containing zinc ions disclosed in Czechoslovakian Inventor's Certificate 264,719:

EXAMPLE B (Example 5 of Czech Inventor's Certificate)

A 0.1% aqueous solution of Na—HY containing zinc ions is prepared by dissolving 10 mg of Na—HY and 0.001 mg of zn($SO_4$). $7H_2O$ in 10 ml of apyrogenic physiological solution.

Method: One ml of the different 0.1% aqueous starting samples was inoculated with 1 ml of the test organisms described herein below and the changing of the number of germs was taken against time.

The number of germs was determined in a point of time by plating method.

Medium applied: Soya-casein agar (Caso-agar [Merck]).

Microorganisms applied: Staphylococcus aureus Salmonella sp.

Starting number of germs: $\Sigma 10^6$/ml

Number of parallel experiments: 3

The solutions applied:

1—aqueous solution of Zn—HY of 0.1% by weight.

2—aqueous solution of Na—HY of 0.1% by weight.

3—aqueous solution of Na—HY containing Zn ions (0.1% by weight) (prepared according to the process described in the Czecho-Slovakian Inventor's Certificate No. 264 719).

The results are shown in Table 1.

As it is shown, in the case of Zn—HY no germs were observed after 48 hours but in the case of Na—HY and Na—HY containing Zn ions the number of germs began to increase after 24 hours.

TABLE 3

| | Staphylococcus aureus | | | Salmonella sp. | | |
|---|---|---|---|---|---|---|
| Time | 1 | 2 | 3 | 1 | 2 | 3 |
| 0 h | $4.2 \times 10^6$ | $1.3 \times 10^6$ | $1.4 \times 10^6$ | $2.0 \times 10^6$ | $8.0 \times 10^6$ | $4.2 \times 10^6$ |
| 2 h | $3.4 \times 10^6$ | $1.4 \times 10^6$ | $1.3 \times 10^6$ | $1.4 \times 10^6$ | $7.0 \times 10^6$ | $4.4 \times 10^6$ |
| 4 h | $3.1 \times 10^6$ | $1.2 \times 10^6$ | $1.3 \times 10^6$ | $1.2 \times 10^6$ | $6.8 \times 10^6$ | $4.2 \times 10^6$ |
| 6 h | $2.4 \times 10^6$ | $1.6 \times 10^6$ | $1.2 \times 10^6$ | $1.0 \times 10^6$ | $6.5 \times 10^6$ | $3.9 \times 10^6$ |
| 1 day | $2.6 \times 10^6$ | $4.1 \times 10^6$ | $2.1 \times 10^6$ | $1.1 \times 10^6$ | $8.1 \times 10^6$ | $6.1 \times 10^6$ |
| 2 day | 0 | $6.2 \times 10^6$ | $4.5 \times 10^6$ | 0 | $1.2 \times 10^6$ | $1.3 \times 10^6$ |
| 3 day | 0 | $8.4 \times 10^6$ | $8.4 \times 10^6$ | 0 | $1.8 \times 10^6$ | $1.7 \times 10^6$ |
| 4 day | 0 | | | 0 | | |
| 7 day | 0 | | | 0 | | |

EXAMPLE C

The test for the antibacterial effect of Co(II)HY has also been carried out and the results are given in the following table. The test was carried out in the same was as in Example A except that E coli was applied as the second microorganism instead of Salmonella sp.

TABLE 4

| | Staphylococcus aureus | | E coli. | |
|---|---|---|---|---|
| Time | 1 | 2 | 1 | 2 |
| 0 h | $3 \times 10^6$ | $1.9 \times 10^6$ | $4.5 \times 10^6$ | $5.8 \times 10^6$ |
| 4 h | $2.1 \times 10^6$ | $7.5 \times 10^5$ | $4.6 \times 10^6$ | $4.5 \times 10^6$ |
| 24 h | $1.3 \times 10^6$ | $3.5 \times 10^6$ | $1.8 \times 10^6$ | $1.0 \times 10^6$ |
| 48 h | $5.8 \times 10^6$ | $1.0 \times 10^6$ | $5.5 \times 10^6$ | $9.0 \times 10^2$ |
| 72 h | $2.8 \times 10^6$ | <10 | $5.5 \times 10^6$ | $1.0 \times 10^2$ |
| 6 days | $1.5 \times 10^6$ | <10 | $1.3 \times 10^6$ | <10 |
| 7 days | $1.6 \times 10^6$ | <10 | $2.5 \times 10^6$ | <10 |

1: Aqueous 0.1% by weight solution of Na-HY.
2. Aqueous 0.1% by weight solution of Co-HY.

Note that in Examples A, B and C, the molecular weight of the hyaluronic acid in each case was 1,850,000 daltons. In our opinion, hyaluronic acid will be expected to function equivalently in the present invention irrespective of whether its molecular weight is as low as 50,000 or as high as 8 to 13 million daltons.

Specific Examples

The invention is illustrated in more detail by the following non limiting Examples.

The protein content of hyaluronate (HA) was determined by using the method of O. H. Lowry [J. Biol. Chem. 193 (1951)]; the viscosity of hyaluronate was measured in an Ostwald's viscometer in a physiological saline solution at 25° C. The value of the intrinsic viscosity extrapolated to "0" concentration, i.e. [η]

$$[\eta]_{25°C.}^{c \to 0\%}$$

is given below. The HA content was determined by using Bitter's method [Anal. Biochem. 4, 330 (1962)].

EXAMPLE 1

Preparation of a zinc hyaluronate solution 40.18 mg of sodium hyaluronate are dissolved in 20.0 ml of twice distilled water. Thus, the starting concentration of hyaluronic acid is 2,009 mg/ml, the equivalent concentration of the solution is $4,241 \times 10^{-3}$ mol. liter ($Na^+$ or hyaluronic acid dimer unit). In the course of the measurement, a zinc chloride solution of 0.05154 mol/liter concentration is added to the reaction mixture through a microburet. The solution is first added in little portions (0.05 ml) and then in larger portions (0.1 to 0.2 ml). The potential change in the solution is measured by using a precision potentiometer with digital display and sodium ion-selective glass and silver/silver chloride electrodes. The titration is continued until the potential measured is not further changed by adding an additional portion of the titrating solution. (The measuring system was calibrated under conditions analogous to the practical measurement).

The selectivity of the sodium ion-selective electrode was observed also in the presence of $Zn^{2+}$ ions in order to control that the potential change in the practical measurement was caused by the liberated $Na^+$ ions and not the $Zn^{2+}$ ions introduced to the solution. A $2.00 \times 10^{-3}$ M sodium chloride solution was titrated by using the zinc chloride titrating solution under conditions similar to the above conditions. On increasing the concentration of $Zn^{2+}$ from 0 up to $4 \times 10^{-3}$ mol/liter a potential increase of about 2 mV was observed whereas the practical measurement showed a change of about 20 mV under similar conditions. Thus, the evaluation had no obstacle. In the course of measurement the increase in the sodium ion activity calculated from the measurement data verified the quantitative formation of the zinc associate.

Preparation of a zinc chloride solution

Since a solution containing zinc chloride in an accurate concentration cannot be prepared by direct weighing in, first a solution with the nearly desired concentration is prepared. On preparing this solution no acid should be used thus it may occur that the zinc chloride weighted in will not completely be dissolved. After sedimentation of the insoluble residue (about 30 minutes) the volumetric flask is filled up to the mark and the solution is filtered through a filter paper.

The accurate concentration of the filtrate is determined by complexometric titration by using buffer 10 and eryochrom black-T indicator. The zinc chloride solution with an accurate concentration of 0.100 mol/liter is prepared by the precise dilution of this solution.

The characteristics of sodium hyaluronate used for the preparation of solution are as follows:

| Molecular weight | 1850000 daltons |
| --- | --- |
| Protein content | 0.07% by wt. |
| UV absorption | |
| $A_{257}^{1\%}$ | 0.133 |
| $A_{280}^{1\%}$ | 0.075 |
| Viscosity $[\eta]_{25° C.}^{c \to 0\%}$ | 13.7 dl/g |
| $HA^x$ | 98.12% by wt. |

$^x$HA = hyaluronic acid (as abbreviated herein).

EXAMPLE 2

Preparation of a solution for dermatologic and cosmetic use 12.5 ml of a zinc chloride solution of 0.100 mol/liter concentration prepared with ion-free water are added to 0.50 g of sodium hyaluronate weighted in a 100 ml volumetric flask. (Another concentration of zinc chloride may also be used but the amount of zinc chloride should be the same.) Sodium hyaluronate is allowed to swell (for 12 hours) in the solution filled up to the mark with ion-free The characteristics of sodium hyaluronate used for preparing the above solution are as follows:

| Viscosity $[\eta]_{25° C.}^{c \to 0\%}$ | 16.5 dl/g |
| --- | --- |
| Protein content | 0.8% by wt. |

EXAMPLE 3

Preparation of a zinc hyaluronate solution for use in injectable solutions.

The operations described in this Example are carried out under sterile conditions.

5.0 ml of a zinc chloride solution of 0.100 mol/liter concentration prepared with twice distilled water (water for injection use, pyrogen-free, sterile) are added to 0.20 g of sodium hyaluronate (of pure powder quality) weighted in a 100 ml volumetric flask, then the volume is filled up to 50 ml with twice distilled water. Sodium hyaluronate is allowed to swell overnight, then dissolved by shaking and the solution filled up to the mark with twice distilled water. The solution obtained is filtered through a membrane filter (0.45/µ pore size) to give a zinc hyaluronate solution of 0.2% by wt./vol.

The characteristics of the sodium hyaluronate used for preparing the above solution are as follows:

| Quality | pure, pyrogen-free |
| --- | --- |
| sterile powder | |
| Molecular Weight | 1850000 |
| Protein content | 0.07% by wt. |
| UV absorption | |
| $A_{257}^{1\%}$ | 0.133 |
| $A_{280}^{1\%}$ | 0.075 |
| HA content | 98.12% by wt. |
| Viscosity $[\eta]_{25° C.}^{c \to 0\%}$ | 13.7 dl/g |

EXAMPLE 4

Preparation of an ion-free zinc hyaluronate solution 600 ml of ethanol of analytical grade are added under stirring to 200 ml of 0.50 % by wt./vol. zinc hyaluronate solution obtained according to Example 2, the precipitated zinc hyaluronate is filtered on a glass filter, washed twice with 50 of ethanol each of the same quality and then dried under reduced pressure. Thus, 0.88 g of zinc hyaluronate is obtained which is used for preparing a 0.50% by wt./vol. zinc hyaluronate solution in the way described in Example 2. The zinc hyaluronate solution obtained does not contain any sodium chloride arising from the reaction between sodium hyaluronate and zinc chloride; thus, it is practically ion-free.

EXAMPLE 5

Preparation of ion-free zinc hyaluronate or its solution for therapeutical use

The operation described in this Example is carried out under sterile conditions.

1500 ml of ethanol (purest quality) are portionwise added to 500 ml of zinc hyaluronate solution prepared according to Example 3 under stirring. After the addition the system is stirred for 30 minutes, the zinc hyaluronate precipitate is filtered on a glass filter, washed 3 times with 100 ml of ethanol (purest quality) each and dried under reduced pressure under mild and sterile conditions.

EXAMPLE 6

Preparation of ion-free zinc hyaluronate 200 ml of 10% by wt. solution of Hyamine® 1622 (puriss) (benzyldimethyl{-2-[2-p-(1,1,3,3-tetramethylbutyl) phenoxy]ethoxy}ethyl-ammonium chloride) are added under stirring to the solution containing 1 g of sodium hyaluronate in 400 ml of twice distilled water. The precipitate i.e. the hyaluronic acid quaternary ammonium associate formed is separated by centrifuging, washed twice with 100 ml of twice distilled water each and again centrifuged. The washed precipitate is dissolved in a solvent couple consisting of 400 ml of 2% by wt./vol. zinc chloride in aqueous solution (pH 5.0 to 5.4) and 400 ml of n-butanol. After allowing to separate the two phases, the aqueous layer containing the dissolved zinc hyaluronate is filtered through a membrane filter (0.45/μ pore size), then zinc hyaluronate is precipitated by adding 3 volumes of ethanol, filtered on a glass filter, washed with ethanol and dried in a nitrogen atmosphere under mild conditions to obtain 0.82 g of zinc hyaluronate.

When necessary, a 0.50 % by wt./vol. solution is prepared from the zinc hyaluronate obtained which is then further purified as described in Example 4. The characteristics of sodium hyaluronate used as starting material are as follows:

| | |
|---|---|
| Viscosity $[\eta]_{25°C.}^{c \to 0\%}$ | 16.5 dl/g |
| Protein Content | 018% by wt./vol. |

Zinc hyaluronate can be prepared as described above also from associates formed from other quaternary ammonium salts. Quaternary salts useful for this purpose are e.g.:

a) carbotetradecyloxymethyl-trimethylammonium chloride (see the Hungarian patent specification No. 188, 537),
b) hexadecylpyridinium chloride,
c) cetylpyridinium chloride,
d) trimethylammonium chloride and the like.

EXAMPLE 7

Preparation of cobalt (II) hyaluronate

The process described in Example 6 is followed, except that the hyaluronic acid quaternary ammonium associate is dissolved in a solvent couple consisting of a 2% by wt./vol. cobalt(II)chloride. $6H_2O$ aqueous solution and n-butanol. The bond lengths are as follows: Co—O: 197 pm±1.0 and Co—C: 239 pm+1.5 pm.

EXAMPLE 8

Preparation of an aqueous solution containing 0.50% by wt./vol. of zinc hyaluronate made isotonic by zinc chloride About 50 ml of a zinc chloride solution of 0.110 mol/liter concentration are added to 0.50 g of sodium hyaluronate in a 100 ml volumetric flask and then allowed to swell overnight. Then, the sodium hyaluronate is dissolved by shaking and the flask is filled up to the mark with a zinc chloride solution of 0.110 mol/liter concentration.

The osmotic pressure of the solution obtained is 0.1491 mol/liter as expressed in equivalent sodium chloride concentration, the value of pH is 5.0. When necessary, the pH value is adjusted to 5.5 to 5.6 by adding 2.00 ml of a sodium acetate solution of 0.150 mol/liter concentration. After adjusting the pH value, the osmotic pressure of the solution is 0.1489 as expressed in equivalent sodium chloride concentration.

The zinc hyaluronate solution is prepared from the particularly pure sodium hyaluronate described in Example 3 with twice distilled water under aseptic conditions, then the solution is filtered through a membrane filter (0.45/μ pore size).

The solution obtained can be used in injectable compositions, too.

EXAMPLE 9

Preparation of an aqueous solution containing 0.2% by wt./vol. of zinc hyaluronate made isotonic by zinc chloride For a final volume of 100 ml, 0.20 g of sodium hyaluronate is weighed in and dissolved in a zinc chloride solution of 0.120 mol/liter concentration.

The dissolution and preparation of the zinc chloride solution of precisely 0.120 mol/liter concentration are carried out according to Example 1 according to the sense by changing the amount of zinc chloride).

The osmotic pressure of the solution is 0.154 mol/liter as expressed in equivalent sodium chloride concentration; the pH shows a value of 5.3 to 5.4.

| | |
|---|---|
| HA content | 1.96 mg/ml |
| Viscosity | 15.9 dl/g |
| Protein concentration | 0.015 mg/ml |
| Purity of the solution$^x$ | $A_{660}^{1\ cm} = 0.015$ |

$^x$Based on the absorbance measured at 660 nm in a 1 cm cuvet.

The solution is prepared by using the sodium hyaluronate of the quality characterized in Example 2 and used first of all for the preparation of dermatologic and cosmetic compositions.

EXAMPLE 10

Preparation of an aqueous solution containing 0.50 % by wt./vol. of zinc hyaluronate made isotonic by glucose The solution of this Example contains sodium hyaluronate and the calculated equivalent amount of zinc chloride.

12.50 ml of a zinc chloride solution of 0.100 mol/liter concentration are added to 0.50 g of sodium hyaluronate weighed in a 100 ml volumetric flask. (Another concentration of zinc chloride may also be used but the amount of zinc chloride should be the same.) Sodium hyaluronate is allowed to swell for 12 hours in the solution of zinc chloride filled up to 50 ml with ion-free water, then dissolved by shaking. Thereafter, 24.50 ml of a glucose solution of 1.00 mol/liter concentration are added and filled up to the mark with ion-free water.

The osmotic pressure of the solution is 0.1495 mol/liter as expressed in equivalent sodium chloride concentration; the pH shows a value of 5.4. Total zinc concentration=$1.25 \times 10^{-2}$ mol/liter.

The solution is prepared by using the sodium hyaluronate of the quality characterized in Example 2 and used first of all for the preparation of dermatological and cosmetic compositions.

EXAMPLE 11

Preparation of an aqueous solution containing 0.2% by wt./vol. of zinc hyaluronate made isotonic by glucose The solution of this example contains sodium hyaluronate and the calculated equivalent amount of zinc chloride.

5.0 ml of a zinc chloride solution of 0.100 mol/liter concentration are added to 0.20 g of sodium hyaluronate weighted in a 100 ml volumetric flask, then the volume is completed to 50 ml with deionized water. After allowing to swell overnight, sodium hyaluronate is dissolved by shaking, 27.0 ml of a glucose solution of 1.00 mol/liter concentration are added and the flask filled up to the mark with ion-free water.

The osmotic pressure of the solution is 0.151 mol/liter as expressed in equivalent sodium chloride concentrations; the pH shows a value of 5.6 to 5.7; Total zinc concentration= $5 \times 10^{-3}$ mol/liter.

EXAMPLE 12

Preparation of an aqueous solution containing 0.5% by wt./vol. of zinc hyaluronate made isotonic by sorbitol The zinc hyaluronate solution described hereinafter is prepared under aseptic conditions from sodium hyaluronate of particularly high purity described in Example 3 and distilled water. The solution contains zinc chloride in an equivalent amount calculated for sodium hyaluronate.

The process described in Example 10 is followed, except that, instead of the glucose solution, 23.50 ml of a sorbitol solution of 1.00 mol/liter concentration (182.19 g of D-sorbitol in 1 liter) are added to the zinc hyaluronate solution.

The solution thus prepared is filtered through a membrane filter (0.45/µ pore size). This solution can be used for any purpose including injectable compositions.

The osmotic pressure of the solution is 0.1520 mol/liter as expressed in equivalent sodium chloride concentration; the pH shows a value of 5.5; Total zinc concentration=$1.25 \times 10^{-2}$ mol/liter.

EXAMPLE 13

Preparation of an aqueous solution containing 0.2% by wt./vol. of zinc hyaluronate made isotonic by sorbitol The solution described in this Example contains zinc chloride in an equivalent amount calculated for sodium hyaluronate.

The zinc hyaluronate solution described hereinafter is prepared under aseptic conditions from sodium hyaluronate of particularly high purity described in Example 3 with twice distilled water.

The process of Example 12 is followed, except that 0.2 g of sodium hyaluronate is dissolved, 5 ml of zinc chloride solution of 0.100 mol/liter concentration, then 26.50 ml of a sorbitol solution of 1 mol/liter concentration are added and finally, the solution is filled up to 100 ml. The solution thus prepared is filtered through a membrane filter (0.45/µ pore size) This solution can be used for any purpose including injectable compositions.

The osmotic pressure of the solution is 0.1501 mol/liter as expressed in equivalent sodium chloride concentration; the pH shows a value of 5.6.

| | |
|---|---|
| Total zone concentration = | $5 \times 10^{-3}$ mol/liter |
| Hyaluronate content | 2.03 mg/ml |
| Viscosity | 16.1 dl/g |
| Protein content | 0.016 mg/ml |
| Purity of the solution* | $A_{660}^{1\ cm} = 0.010$ |

*Based on the absorbance measured at 660 nm in a 1 cm cuvet.

EXAMPLES 14 to 26

In the following the components of various compositions (pharmaceutical and cosmetic compositions) are given in relation to formulation types selected by us. The preparation of zinc hyaluronate solutions made isotonic are described in the preceding Examples. Here, "distilled water for injection purposes" means twice distilled water prepared under aseptic conditions.

I. INJECTABLE SOLUTIONS

Compositions of Examples 14 to 17 are used for intracutaneous administration whereas that of Example 18 serves for intraocular use. The active ingredient of the quality described in Example 3 is employed in these Examples.

EXAMPLE 14

| | |
|---|---|
| Zinc hyaluronate active ingredient | 2.0 mg |
| Sorbitol | 48.3 mg |
| Final volume of the aqueous solution prepared with distilled water for injection purposes | 1.0 ml |

EXAMPLE 15

| | |
|---|---|
| Zinc hyaluronate active ingredient | 5.0 mg |
| Sorbitol | 42.8 mg |
| Final volume of the aqueous solution prepared with distilled water for injection purposes | 1.0 ml |

EXAMPLE 16

| | |
|---|---|
| Zinc hyaluronate active ingredient | 2.0 mg |
| Propyl p-hydroxybenzoate | 0.05 mg |
| Methyl p-hydroxybenzoate | 0.5 mg |
| Glucose | 48.6 mg |
| Final volume of the aqueous solution prepared with distilled water for injection purposes | 1.0 ml |

EXAMPLE 17

| | |
|---|---|
| Zinc hyaluronate active ingredient | 5.0 mg |
| Propyl p-hydroxybenzoate | 0.05 mg |
| Methyl p-hydroxybenzoate | 0.5 mg |
| Glucose | 44.1 mg |
| Final volume of the aqueous solution prepared with distilled water for injection purposes | 1.8 ml |

EXAMPLE 18

| | |
|---|---|
| Zinc hyaluronate active ingredient | 10.0 mg |
| Potassium sorbate | 1.0 mg |
| Sorbitol | 41.0 mg |
| Final volume of the aqueous solution prepared with distilled water for injection purposes | 1.0 ml |

Compositions described in Examples 20 to 28 are mainly used for dermatologic and cosmetic purposes. The active ingredient of the quality described in Example 2 is employed in these Examples.

II. SOLUTIONS FOR TOPICAL USE

EXAMPLE 19

| | |
|---|---|
| Zinc hyaluronate active ingredient | 5.0 mg |
| Potassium sorbate | 1.0 mg |
| Sodium acetate | 24.6 mg |
| Final volume of the aqueous solution | 1.0 ml |

-continued

| | |
|---|---|
| prepared with distilled water | |

EXAMPLE 20

| | |
|---|---|
| Zinc hyaluronate active ingredient | 2.0 mg |
| Potassium sorbate | 1.0 mg |
| Sorbitol | 48.3 mg |
| Final volume of the aqueous solution prepared with distilled water | 1.0 ml |

III. GELS FOR TOPICAL USE

EXAMPLE 21

| | |
|---|---|
| Zinc hyaluronate active ingredient | 20.0 mg |
| Acrylic acid polymerisate | 200 mg |
| Sodium hydroxide of 30% concentration | 50 mg |
| Potassium sorbate | 10 mg |
| Distilled water     up to | 10.0 mg |

EXAMPLE 22

| | |
|---|---|
| Zinc hyaluronate active ingredient | 20.0 mg |
| Acrylic acid polymerisate | 50 mg |
| Sodium hydroxide of 30% concentration | 40 mg |
| Propylene glycol | 1500 mg |
| Potassium sorbate | 10 mg |
| Distilled water     up to | 10.0 mg |

IV. CREAMS AND OINTMENTS FOR TOPICAL USE

EXAMPLE 23

| | |
|---|---|
| Zinc hyaluronate active ingredient | 50 mg |
| Potassium sorbate | 10 mg |
| Soft white bee wax | 125 mg |
| Sorbitan oleate | 150 mg |
| Cetyl stearyl alcohol | 840 mg |
| Glyceryl monostearate | 1100 mg |
| Propylene glycol | 4750 mg |
| Distilled water     up to | 10 mg |

EXAMPLE 24

| | |
|---|---|
| Cobalt hyaluronate active ingredient | 50 mg |
| Potassium sorbate | 10 mg |
| Soft white bee wax | 125 mg |
| Sorbitan oleate | 150 mg |
| Cetyl stearyl alcohol | 840 mg |
| Glyceryl monostearate | 1100 mg |
| Propylene glycol | 4750 mg |
| Distilled water     up to | 10 mg |

EXAMPLE 25

| | |
|---|---|
| Zinc hyaluronate active ingredient | 50 mg |
| 2-Phenoxyethanol | 100 mg |
| Sodium lauryl sulfate | 100 mg |
| Cetyl palmitate | 400 mg |
| Stearin | 400 mg |
| Stearyl alcohol | 450 mg |
| Cetyl alcohol | 450 mg |
| White vaseline | 500 mg |
| Propylene glycol | 550 mg |
| Glycerol | 600 mg |
| Distilled water     up to | 10.0 mg |

EXAMPLE 26

| | |
|---|---|
| Cobalt(II)hyaluronate active ingredient | 50 mg |
| 2-Phenoxyethanol | 100 mg |
| Sodium lauryl sulfate | 100 mg |
| Cetyl palmitate | 400 mg |
| Stearin | 400 mg |
| Stearyl alcohol | 450 mg |
| Cetyl alcohol | 450 mg |
| White vaseline | 500 mg |
| Propylene glycol | 550 mg |
| Glycerol | 600 mg |
| Distilled water     up to | 10.0 mg |

EXAMPLE 27

| | |
|---|---|
| Zinc hyaluronate active ingredient | 50.0 mg |
| Microcrystalline wax | 250 mg |
| Propylene glycol | 500 mg |
| Sorbitol | 400 mg |
| Wool wax (acetylated) | 500 mg |
| White vaseline     up to | 10 g |

V. COMPOSITIONS FOR THE PURIFICATION AND CICATRIZATION OF PURULENT WOUNDS AND BURNS

EXAMPLE 28

| | |
|---|---|
| Zinc hyaluronate active ingredient | 10 mg |
| Potassium sorbate | 1.0 mg |
| Hydrophilic colloidal silicon dioxide | 50 mg |
| Sorbitol     up to | 1 mg |

What is claimed is:

1. A stoichiometric cobalt(II) hyaluronic acid complex prepared through the interaction of equivalent amounts of an alkali metal hyaluronate, alkaline earth metal hyaluronate, silver hyaluronate or quaternary ammonium hyaluronate, and Co(II) ions in aqueous solution wherein the cobalt(II) is surrounded by four oxygen atoms, in the first coordination sphere, the length of the Co—O bond distance is 197 pm±1.0 pm whereas two carbon atoms are present in a longer distance of 239 pm+1.5 pm from the cobalt atom.

2. A pharmaceutical or cosmetic composition for local administration, which comprises as active ingredient, a pharmaceutically or cosmetically effective amount of a stoichiometric cobalt(II) hyaluronic acid complex prepared through the interaction of equivalent amounts of an alkali metal hyaluronate, alkaline earth metal hyaluronate, silver hyaluronate or quaternary ammonium hyaluronate, and Co(II) ions in aqueous solution wherein the cobalt(II) is surrounded by four oxygen atoms, in the first coordination sphere, the length of the Co—O bond distance is 197 pm±1.0 pm whereas two carbon atoms are present in a longer distance of 239 pm+1.5 pm from the cobalt atom and a pharmaceutically acceptable inert carrier.

3. The stoichiometric cobalt(II) hyaluronic acid complex defined in claim 1 prepared through the interaction of equivalent amounts of sodium hyaluronate and Co(II) ions in aqueous solution.

* * * * *